United States Patent [19]
Terwilliger

[11] Patent Number: 5,823,970
[45] Date of Patent: Oct. 20, 1998

[54] BIOPSY NEEDLE SET

[75] Inventor: Richard A. Terwilliger, Estes Park, Colo.

[73] Assignee: Medical Device Technologies, Inc., Gainesville, Fla.

[21] Appl. No.: 619,389

[22] Filed: Mar. 22, 1996

[51] Int. Cl.$^6$ .................................................. A67B 10/00
[52] U.S. Cl. .................... 600/564; 600/567; 604/164; 606/167; 606/170; 606/185
[58] Field of Search ...................... 128/749, 751, 128/753, 754, 757; 606/167, 184, 185, 170; 604/165, 164; 600/564, 562, 565, 566, 567

[56] References Cited

U.S. PATENT DOCUMENTS

| | | |
|---|---|---|
| Re. 34,056 | 9/1992 | Lindgren et al. . |
| 737,293 | 8/1903 | Summerfeldt ........................... 128/751 |
| 1,663,761 | 3/1928 | Hohnson ................................. 128/751 |
| 3,090,384 | 5/1963 | Baldwin et al. . |
| 3,732,858 | 5/1973 | Banko . |
| 3,788,320 | 1/1974 | Dye . |
| 3,844,272 | 10/1974 | Banko . |
| 4,210,146 | 7/1980 | Banko . |
| 4,266,555 | 5/1981 | Jamshidi . |
| 4,403,617 | 9/1983 | Tretinyak . |
| 4,476,864 | 10/1984 | Tezel . |
| 4,570,632 | 2/1986 | Woods . |
| 4,600,014 | 7/1986 | Beraha . |
| 4,640,296 | 2/1987 | Schnepp-Pesch et al. . |
| 4,651,752 | 3/1987 | Fuerst . |
| 4,655,226 | 4/1987 | Lee . |
| 4,699,154 | 10/1987 | Lindgren . |
| 4,733,671 | 3/1988 | Mehl . |
| 4,747,414 | 5/1988 | Brossel . |
| 4,776,346 | 10/1988 | Beraha et al. . |
| 4,817,631 | 4/1989 | Schnepp-Pesch et al. . |
| 4,924,878 | 5/1990 | Nottke . |
| 4,958,625 | 9/1990 | Bates et al. . |
| 5,025,797 | 6/1991 | Baran . |
| 5,064,411 | 11/1991 | Gordon, III . |
| 5,217,479 | 6/1993 | Shuler ..................................... 128/751 |
| 5,220,926 | 6/1993 | Jones . |
| 5,320,110 | 6/1994 | Wang ..................................... 128/753 |
| 5,394,887 | 3/1995 | Haaga ..................................... 128/749 |
| 5,423,844 | 6/1995 | Miller ..................................... 128/751 |
| 5,487,392 | 1/1996 | Haagfa ..................................... 128/751 |
| 5,595,186 | 1/1997 | Rubinstein et al. .................... 128/754 |

FOREIGN PATENT DOCUMENTS

| | | |
|---|---|---|
| 0010321 | 4/1980 | Germany . |
| 0141108 | 4/1980 | Germany . |
| 159394 A | 3/1983 | Germany . |
| 0221 007 A1 | 5/1987 | Germany . |
| 287 650 A5 | 3/1991 | Germany . |
| 175611 | 9/1965 | Russian Federation . |
| 1551362 A1 | 3/1990 | Russian Federation . |
| 1809758 | 4/1993 | U.S.S.R. ................................ 128/751 |
| 709714 | 6/1954 | United Kingdom . |
| 748451 | 5/1956 | United Kingdom . |
| WO 83/03343 | 10/1983 | WIPO . |

*Primary Examiner*—Richard J. Apley
*Assistant Examiner*—Justine R. Yu
*Attorney, Agent, or Firm*—Fliesler, Dubb, Meyer & Lovejoy

[57] ABSTRACT

A biopsy needle set 10 comprises an outer cannula 1 and an inner cannula 2. The outer cannula 1 includes an outer opening 14 and the inner cannula 2 includes an inner opening 12. The inner cannula 2 is rotatable relative to the outer cannula 1 such that the needle set 10 has an opened position wherein the inner opening 12 is located adjacent to the outer opening 14, and a closed position wherein the outer cannula 1 covers the inner opening 12. The needle set, in a closed position, can be inserted into a body in order to collect a tissue sample. Once properly inserted, the needle set can be moved to an opened position and then either selectively further inserted and closed to collect the tissue sample or closed to collect the tissue sample.

13 Claims, 3 Drawing Sheets

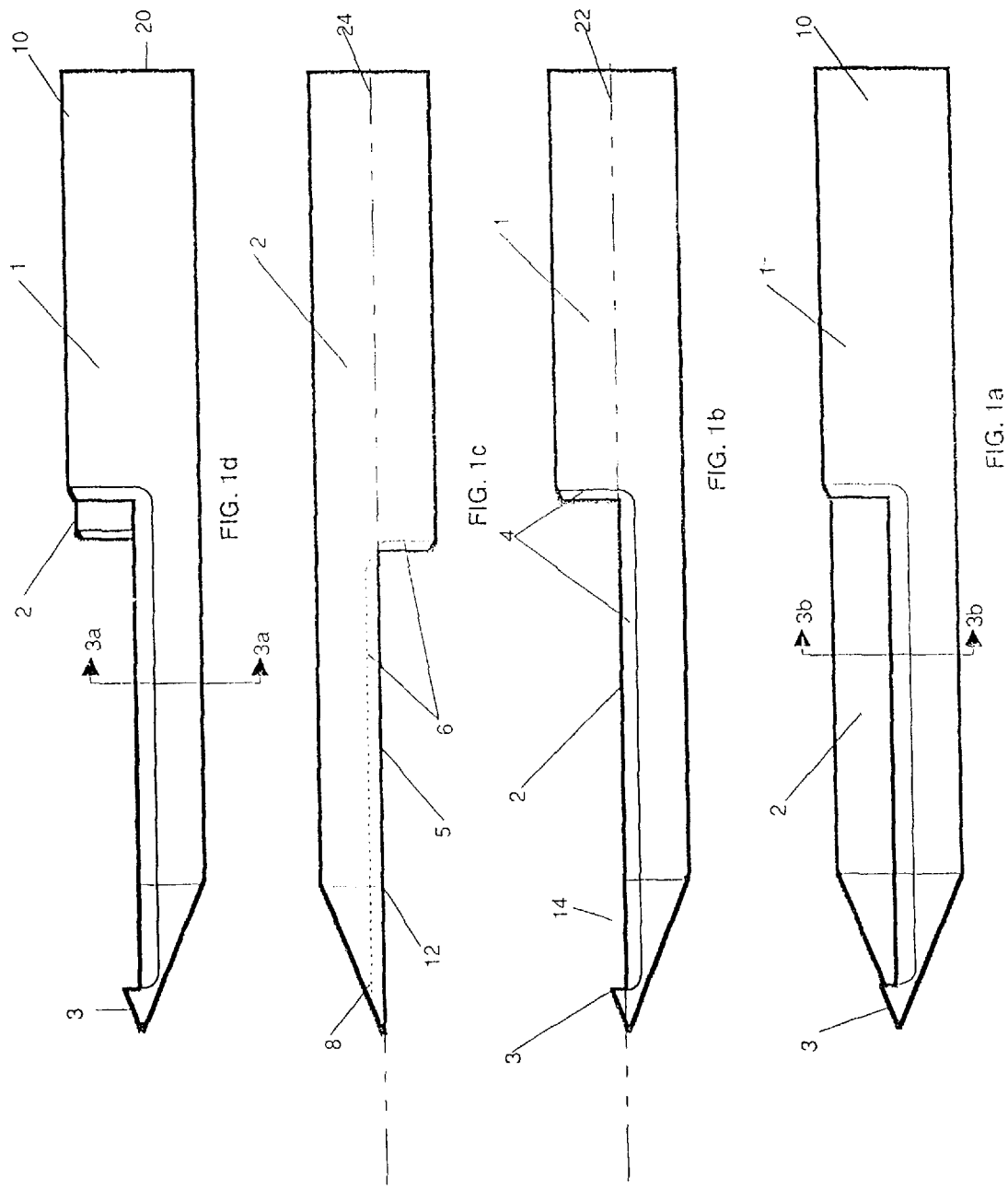

BIOPSY NEEDLE SET

BACKGROUND

1. Field of the Invention

This invention relates to an improved method to collect a tissue sample from humans or animals by a procedure referred to as tissue biopsy, and more particularly to an improved needle design which allows a more reliable way to obtain large tissue cores while performing tissue extraction from a tissue mass in a precise and rapid manner with minimum patient discomfort.

2. Background of the Invention

It is often desirable and frequently absolutely necessary to sample or test a portion of tissue from humans and even animals to aid in the diagnosis and treatment of patients with cancerous tumors, premalignant conditions and other diseases or disorders. Typically in the case of cancer or the suspicion of malignant tumors, a very important process call tissue biopsy is performed to establish whether cells are cancerous.

Biopsy may be done by an open or closed technique. Open biopsy removes the entire tissue mass or a part of the tissue mass. Closed biopsy on the other hand is usually performed with a needle-like instrument and may be either an aspiration (hollow needle on a syringe) or a core biopsy (special tissue cutting needle design). In needle aspiration biopsy, individual cells or clusters of cells are obtained for cytologic examination. In core biopsy, a segment of tissue is obtained for histologic examination which may be done as a frozen section or paraffin section.

The methods and procedures of obtaining tissue samples for cytologic or histologic examination have been performed historically by manual insertion and manipulation of the needle. These procedures are performed "blind" by the physician and guided by "feel" and known anatomic "landmarks".

Tumors are first noted in a patient by one of three ways: palpation, x-ray imaging, or ultrasound imaging. Once a tumor is identified, a biopsy procedure is performed. Modern medical opinion dictates early detection of cancer to increase the likelihood of successful treatment. The Automated Core Biopsy Device (ACBD) allows biopsy to be performed on "Tumor Masses" as small as 2 millimeters in diameter. This procedure is performed under ultrasound or x-ray guidance. Tumors of this size cannot be biopsied reliably by hand since the tumor is about the same size as the biopsy needle. Manual attempts at biopsy pushes the tumor away without piercing the mass. Automatic puncture devices accelerate the needle at such a velocity that even a small tumor can be pierced.

Two very important innovations in the field of medical technology have influenced the field of tissue biopsy in the last five years. One, the use of tissue imaging devices which allow the physician to "see" inside the body and visually guide the needle to the tumor mass. Two, the invention of the Automatic Core Biopsy Device (ACBD). The ACBD is an instrument which propels a needle set with considerable force and speed to pierce the tumor mass and collect the tissue sample. This ACBD device has allowed physicians to test tissue masses in the early stages of growth and has contributed to the medical trend of early diagnosis and successful treatment of cancer.

Examples of such ACBD devices have been described and used for obtaining tissue samples in U.S. Pat. Nos. 4,651,752; 4,702,260; and 4,243,048.

These devices on the market are referred to as "biopsy guns". Historically, Automated Core Biopsy Devices (ACBD) have used the "Tru-Cut" needle set design. The "Tru-Cut" needle is comprised of an inner notched stylet with an outer cannula. A stylet is advanced into the tissue under spring power followed by the cannula which cuts and traps the tissue sample in the notch of the stylet. The "Tru-Cut" needle yields a core sample which is semi-circular in cross section, with length of the sample determined by the stroke of the ACBD.

The stylet is a needle with a notched cutout at the distal end. The cannula is a hollow needle with an angled cutting surface at the distal end which slides over the stylet. When the stylet is pushed into tissue, the tissue is pierced and relaxes into the notched cutout. Since the stylet tip is the full diameter of the needle body the tissue must travel over the top of the stylet tip and then down into the notched cutout. When the cannula is slid forward, the tissue in the notch of the stylet is sliced off and retained in the notch until the cannula is drawn back.

The most common "Tru-Cut" needle size used by an ACBD is 18 gauge. The use of 18 gauge needles is a compromise between the physician's desire to use the smallest least invasive needle gauge and the pathologist's needs for as large a tissue sample as possible to minimize false-positive diagnosis. This compromise in needle size leads the physician to obtain multiple core samples from the biopsy site to allow the pathologist sufficient tissue for a solid diagnosis.

The requirements of the physician and the pathologist have dictated the need for an alternative approach in the function and design of the ACBD device and needle sets.

Recently a series of ACBD products have come into the marketplace that have attempted to offer an improved method of core retrieval. They utilize a different method of obtaining core sample than the "Tru-Cut" needle design. These devices accelerate a single hollow cannula forward into the tissue to obtain a fully circular core of tissue. They are referred to as "End Coring" biopsy gun devices.

All of these "End Coring" prior art devices have exhibited inherent problems in their performance. Successful core retrieval has been a major problem. These devices do not reliably obtain a core in each attempt to obtain a core sample of tissue. The major cause of not obtaining a core during a biopsy attempt with these "End Coring" devices is that after the cannula stops inside the body, the cored tissue residing inside the diameter of the cannula is still attached to the surrounding tissue at the distal end of the cannula and is not removed with the cannula.

Current "End Coring" devices attempt to tear off the captured tissue at the end of the cannula by creating a vacuum inside the device which holds the proximal end of the tissue core up inside the bore of the cannula. As the cannula is withdrawn, the captured core tears off from the surrounding tissue. This tearing of tissue can limit the use of these devices to biopsy sites that have soft and unstructured tissues.

This may create a problem for the physician where he must make repeated passes to obtain adequate tissue material for the pathologist to make his diagnosis.

SUMMARY OF THE INVENTION

Accordingly it is a principle object of this invention to provide an improved tissue sampling needle that effectively cut the core off and captures the tissue at the distal end of the cannula.

It is a further object of this invention to function in such a manner as to more reliably obtain tissue samples which have a fully circular cross-section from all types of tissue.

It is a further object of this invention to function in such a manner as to obtain tissue samples which are significantly longer than the length of forward motion of the needle set from all types of tissue.

It is a further object of this invention to allow less invasive procedures to be performed by reducing the number of attempts necessary to obtain diagnostic material, thus reducing tissue trauma, while allowing the maximum tissue to be harvested with the minimum number of samples taken.

It is a further object of this invention to provide a biopsy needle design which overcomes the problems of existing "End Coring" devices to allow a more reliable means of obtaining core samples for every attempt.

It is a further object of this invention to provide a biopsy instrument whose needle tip design will facilitate the cutting and separation of the tissue core from the surrounding tissue.

These and other objects of the invention will be apparent from the following descriptions and claims.

Based on the prior art instruments for biopsy sampling of tissue masses and the actual present state of this art, there exists a need for an instrument which can reliably obtain biopsy samples which yield more tissue volume for a given needle gauge than currently marketed devices. This increased tissue volume allows the physician to use smaller needle gauges and/or reduce the number of punctures per biopsy site.

The ability to use smaller needle gauges and/or less punctures per biopsy site, opens up the other major areas of biopsy procedures to the use of a device which will increase the reliability and safety of these procedures.

Accordingly, I have invented a needle design for removing cylindrically shaped tissue samples of pre-determined size from a tissue mass for examination.

The needle set 10 may be used in a spring powered mechanical design or other method of operation of its major components. The needle set consists of a outer hollow cannula 1 with an inventive grind 4 and an inner hollow cannula 2 with a similar inventive grind 6. Both cannulas are hollow with tapered conical closed tip 3, 11 at the distal end.

The inner cannula 2 is positioned coaxially inside the outer cannula 1. The outer cannula 1 and the inner cannula 2 can be created in a preferred embodiment using two pencil pointed needles, which are commercially available. The pencil pointed needle that is to form the inner cannula fits inside, the pencil pointed needle that is to form the outer cannula. At the distal end of both pencil pointed needles, approximately one half of the needle diameter has been ground away exposing the inner diameter of the needle and defining openings 2, 5. The edges of these openings 2, 5 are sharpened to accommodate the cutting and severing of the tissue during operation of the cannulas of the needle set 10. Since approximately one half of the needle diameter has been ground away, tissue that is entering into the exposed cutout, must only flow into the opening created by the needle grind without the need to travel over the top of the full diameter of the needle body as is necessary in prior art designs.

In the appropriate orientation, with the ground cutouts opposing each other, the two needles placed coaxially, form a closed pointed tip which facilitates the introduction of the needle set into the tissue mass while preventing tissue from entering the cannulas as the needle set is introduced into the body.

In a preferred form, the tissue is penetrated by the forward motion of the cannulas in the closed position into the tissue. At the appropriate site that a biopsy is required, the inner cannula 2 is rotated to an open position such that the opening 12 is aligned with the outer cannula opening 14. The needle set 10 is then rapidly advanced into the tissue and the tissue moves up into the rotated hollow bore of the inner cannula 2 by the forward motion of the cannulas. The cannulas 1, 2 in the open position, advance a defined distance into the tissue. At the end of the forward motion of the cannulas, the inner cannula 2 is rotated approximately 180°, about colinear longitudinal axes 22, 24, to close the needle set 10. The captured tissue in the enclosed cavity 16 created by the rotation of the inner cannula adds to the overall length of the complete core. The length of the tissue core will be the combined total of forward motion of the needle set 10 plus the length of the ground openings 12, 14 of the cannulas 1, 2. It is therefore possible to obtain a core with an overall length that is twice the distance traveled by the needle set alone.

After the needle set is withdrawn from the body, the inner cannula is rotated open and a mandrel 18 inside the inner cannula is pushed forward to remove the captured core 7 of tissue.

In another preferred form, it may be desired not to have the needle set 10 rapidly moved through the tissue. In this situation, the tissue is penetrated by the forward motion of the cannulas 1, 2 in the closed position to the appropriate site a biopsy is required. The inner cannula 2 is then rotated to an open position such that the opening 12 is aligned with the opening 14 of the outer cannula 1. The surrounding tissue prolapses or sags into the hollow bore of the inner cannula 2 and the inner cannula 2 is rotated approximately 180° to close the needle set. The captured tissue in the enclosed cavity created by the rotation of the inner cannula 2 describes the overall length of the tissue core.

After the needle set 10 is withdrawn from the body, the inner cannula 2 is rotated open and a mandrel 18 inside the inner cannula is pushed forward to remove the captured core 7 of tissue.

In another preferred form, It may be desired not to have the needle set rapidly moved through the tissue, but also to remove the core without removing the complete needle set from the body. In this situation, the tissue is penetrated by the forward motion of the cannulas 1, 2 in the closed position to the appropriate site a biopsy is required. Then the inner cannula is rotated to an open position such that the opening 12 is aligned with the opening 14 of the outer cannula 1. The surrounding tissue prolapses or sags into the hollow bore of the inner cannula 2 and the inner cannula 2 is rotated approximately 180° to close the needle set. The captured tissue in the enclosed cavity created by the rotation of the inner cannula describes the overall length of the tissue core.

To remove the core 7 from the body of the patient, the inner cannula 2 of the needle set 10 is withdrawn out the proximal end 20 of the outer cannula 1. The inner cannula 2 pulls the captured core 7 of tissue back out of the outer cannula and can then be removed. If desired, the inner cannula 2 can then be reinserted coaxially back into the outer cannula 1. Then, the needle set 10 can be rotated or otherwise reoriented and an additional core can be obtained through the initial puncture site thus precluding the necessity of multiple puncture sites for multiple core samples.

BRIEF DESCRIPTION OF THE DRAWINGS

The above noted advantages and other characteristic features of the present invention will be apparent from the accompanying drawings, and in part pointed out in the following detailed description of the preferred embodiment of the invention in which references will be made to the accompanying drawings wherein like reference numerals designate corresponding parts and wherein;

FIG. 1a is a side elevation view of the distal end of the biopsy needle set of this invention, and depicts the device in the "closed" position.

FIG. 1b, is a side elevation view of the distal end of the outer cannula of this invention.

FIG. 1c is a side elevation view of the distal end of the inner cannula of this invention.

FIG. 1d is a side elevation view of the distal end of the biopsy needle set of this invention, and depicts the device in the "open" position.

FIG. 3b is a cross-sectioned view taken through line 3b—3b in FIG. 1a.

DESCRIPTION OF THE PREFERRED EMBODIMENT

Figure 1E:
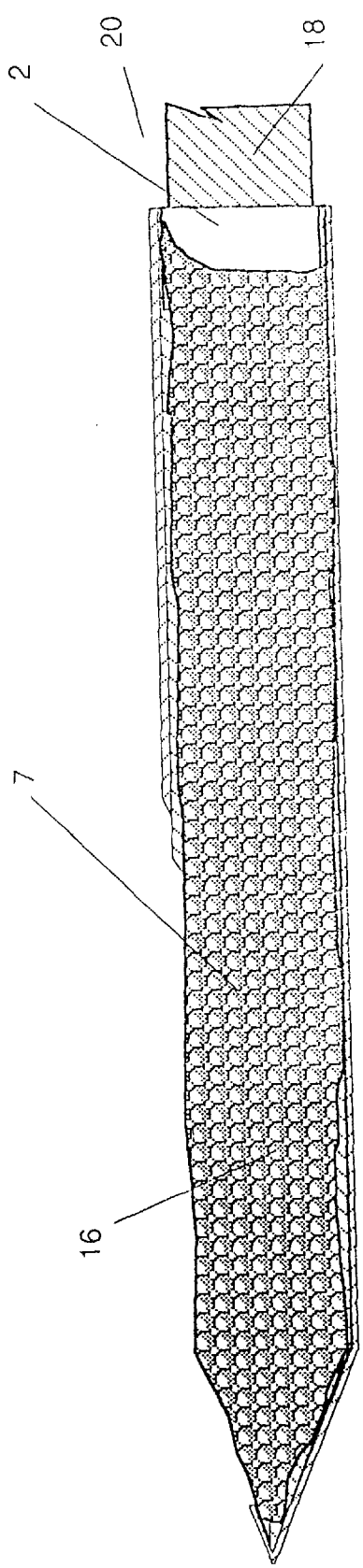
FIG. 1e is a cross-sectioned side elevation view of the distal end of the biopsy needle set of this invention depicted in the "open" position of FIG. 1d with a captured core positioned inside the cannulas.

For the purposes of promoting an understanding of the principles of the invention, reference will now be made to the embodiment illustrated in the drawings and specific language will be used to describe the same. It will nevertheless be understood that no limitation of the scope of the invention is thereby intended, as alterations and further modifications and applications of the principles of the invention as described and illustrated would be contemplated and would occur to one skilled in the art to which the invention relates.

Considering now the drawings, FIGS. 1a, 1b, 1c, 1d, and 1e in detail. These drawings depict side elevation views of the embodiment is of the inventive biopsy needle set. These drawings depict the major components of said embodiment tissue piercing and removal device.

Considering now the drawings, FIGS. 1a, 1b, 1c, 1d, and 1e in detail. These drawings depict views of the embodiment of the inventive cannula tip grind of the biopsy instrument.

In FIG. 1a, the inventive grind and tip of the outer cannula 1 and inner cannula 2 of the needle set 10 are shown.

In FIG. 1b, a side elevation view of outer cannula 1 (with longitudinal axis 22), is shown with the grind to create opening 2. The grinding of opening 2, creates the capture tip 3, that holds the conical tip 8 of inner cannula 2 (with longitudinal axis 24) in place during rotating and cutting. The sharpened edges or grind 4 on cannula 1 cut the tissue during the needle set operation.

In FIG. 1c, a side elevation view of inner cannula 2, is shown with the grind 6 to create opening 5. The grind 6 of opening 5 seats into the capture tip 3, of outer cannula 1. This allows inner cannula 2 to remain in place during rotating and cutting. The sharpened edges or grind 6 on inner cannula 2 cut the tissue during the needle set operation.

In FIG. 1d, a side elevation view of outer cannula 1 and inner cannula 2 are shown in the open position. In this position outer cannula 1 and inner cannula 2 may be pushed forward into the surrounding tissue to obtain a tissue core.

In FIG. 1e, a cross-sectioned side elevation view, is shown with a tissue core, 7 in place between outer cannula and inner of the needle set 10 in cannula 2.

Figure 3B:
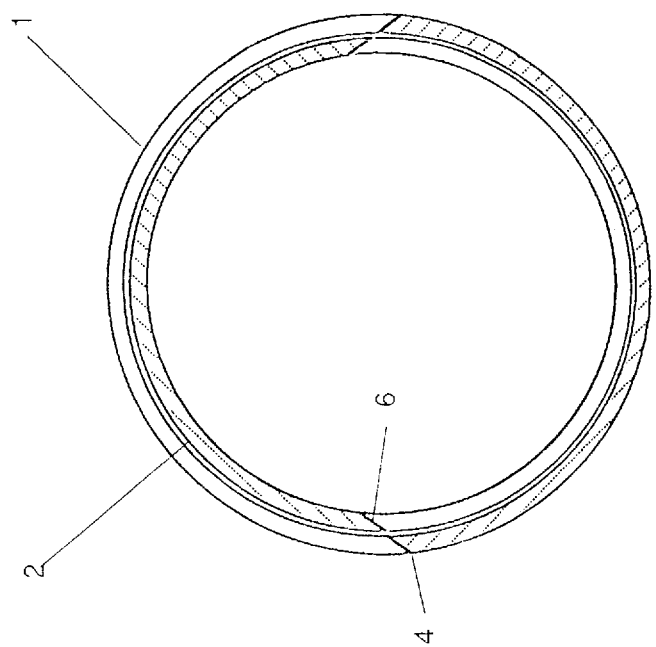
Figure 3A:
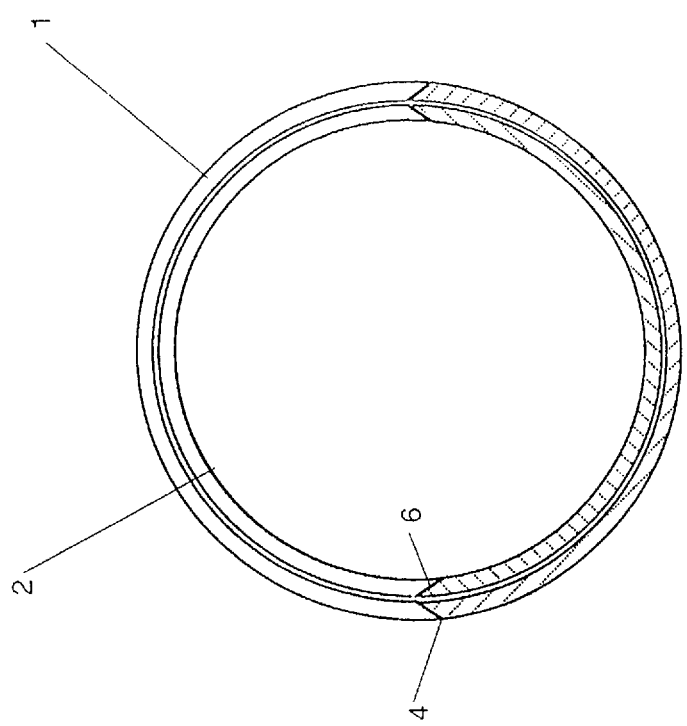
FIG. 3a is a cross-sectioned view taken through line 3a—3a in FIG. 1d.

In FIGS. 3a, 3b, the grinds 4, 6 are shown in one orientation with respect to each other. Other orientations are within the spirit and scope of the invention. For example, in FIG. 3a, the grinds 4, 6 slope towards each other. In a similar figure for another embodiment, the grinds could be parallel to each other and slope in a number of directions.

Figure 2A:
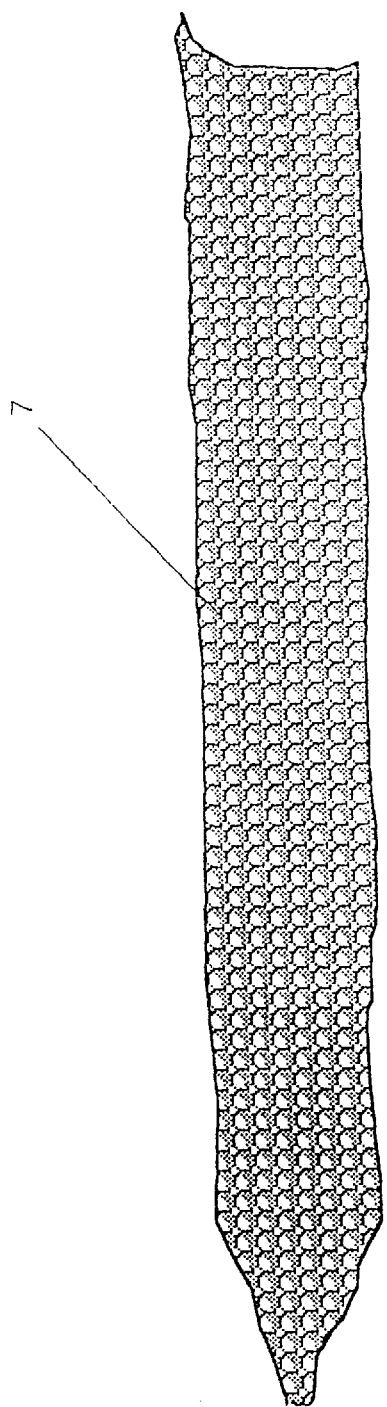
FIG. 2 is a cross-sectional side elevation view of the tissue harvested in FIG. 1e.

In FIG. 2, the tissue core 7, is shown after it is removed from the needle set 10.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

I claim:

1. A biopsy needle set comprising:

an outer cannula;

an inner cannula;

said outer cannula having an outer distal end with an outer opening;

said inner cannula having an inner distal end with an inner opening;

said inner cannula rotatably mounted inside said outer cannula;

said needle set having an open position wherein said inner opening is located adjacent said outer opening, and a closed position wherein said outer cannula covers the inner opening;

said outer cannula has a first longitudinal axis;

said inner cannula has a second longitudinal axis;

said inner cannula is rotatably mounted about the second longitudinal axis;

said outer cannula has an outer distal pointed tip;

said inner cannula has an inner distal pointed tip which mates inside of the outer distal pointed tip and is held in place inside the outer distal pointed tip in order to allow the inner cannula and the outer cannula to rotate relative to each other;

said outer opening of said outer cannula has a first cutting edge thereon;

said inner opening of said inner cannula has a second cutting edge thereon;

wherein said first cutting edge is provided down to approximately the first longitudinal axis at the outer distal pointed tip of the outer cannula and said second cutting edge is provided down to approximately the second longitudinal axis at the inner distal pointed tip of the inner cannula so that with the needle set in said open position, the inner distal pointed tip nests inside of the outer distal pointed tip; and wherein the first and second cutting edge are without serrations in order to facilitate the slicing off of tissue as the needle set is urged past tissue along a direction co-linear with the first and second longitudinal axis.

2. The needle set of claim 1 wherein:

said outer cannula is made from a first pencil pointed needle; and said inner cannula is made from a second pencil pointed needle which fits inside of the first pencil pointed needle.

3. The needle set of claim 2 wherein:

the pencil pointed needle has said outer opening provided therein on a portion located at the outer distal end; and the second pencil pointed needle has the inner opening provided therein on a portion located at the inner distal end.

4. The needle set of claim 1 further including:

a mandrel located inside of the inner cannula so as to be movable along said second longitudinal axis of said inner cannula.

5. The needle set of claim 1 wherein:

said first cutting edge and said second cutting edge are oriented so that, in a plane which is substantially perpendicular to the first and second longitudinal axes, said edges slope toward each other in order, together, to form a "V" shaped edge.

6. A method of making a needle set comprising the steps of:

selecting a first needle with a first longitudinal body, having a first longitudinal axis, and a first distal end;

selecting a second needle with a second longitudinal body, having a second longitudinal axis that is co-linear with the first longitudinal axis, and a second distal end, which second needle that fits inside and is rotatable inside of the first needle;

creating a first opening In said first longitudinal body adjacent to the first distal end, wherein said first opening extends to approximately one half of a diameter of said first longitudinal body at said first distal end;

creating a second opening In said second longitudinal body adjacent to the second distal, wherein said second opening extends to approximately one half of a diameter of said second longitudinal body at said second distal end;

with the needle set in an open position pursuant to the rotation of the first needle relative to the second needle, ensuring that the first opening is adjacent to the second opening;

with the needle set in a closed position pursuant to the rotation of the first needle relative to the second needle, ensuring that the first longitudinal body covers the second opening;

selecting said first needle to be a first pencil pointed needle, with the first opening extending through the first distal end of the first pencil pointed needle;

selecting said second needle to be a second pencil pointed needle with the second opening extending through the second distal end of the second pencil pointed needle;

providing a first edge on said first opening which first edge is without serrations; and providing a second edge on said second opening which second edge is without serrations.

7. A method of making a biopsy of tissue in a body including the steps of:

selecting a needle set which includes:

(a) an outer cannula;

(b) an inner cannula;

(c) said outer cannula having an outer distal end with an outer opening;

(d) said inner cannula having an inner distal end with an inner opening;

(e) said inner cannula rotatably mounted inside said outer cannula; and (f) said needle set having an open position wherein said inner opening Is located adjacent said outer opening, and a closed position wherein said outer cannula covers the inner opening;

(g) said outer cannula has a first longitudinal axis;

(h) said inner cannula has a second longitudinal axis;

(i) said inner cannula is rotatably mounted about the second longitudinal axis;

(j) said outer cannula has an outer distal pointed tip;

(k) said inner cannula has an inner distal pointed tip which mates inside of the outer distal pointed tip and is held in place inside the outer distal pointed tip in order to allow the inner cannula and the outer cannula to rotate relative to each other;

(l) said outer opening of said outer cannula has a first cutting edge thereon;

(m) said inner opening of said inner cannula has a second cutting edge thereon;

(n) wherein said first cutting edge is provided down to approximately the first longitudinal axis at the outer distal pointed tip of the outer cannula and said second cutting edge is provided down to approximately the second longitudinal axis at the inner distal pointed tip of the inner cannula so that with the needle set in said open position, the inner distal pointed tip nests inside of the outer distal pointed tip;

inserting said needle set in the body;

said inserting step includes inserting the needle set into the body adjacent to the tissue to be samples;

positioning the needle set in the open position;

allowing tissue to relax into the needle set;

said inserting step then including further inserting the needle set into the body to capture tissue in the needle set as the needle set is being further inserted into the body in order to capture a tissue sample that is longer than the inner opening of the inner cannula; and positioning said needle set in the closed position by rotating said inner cannula to sever the captured tissue.

8. The method of claim 7 including the steps of:

removing the needle set from the body;

positioning the needle set to the open position; and using a mandrel located in the inner cannula to force out the tissue sample.

9. The method of claim 7 including the steps of:

pulling the inner cannula longitudinally out of the outer cannula in order to have access to the tissue sample.

10. The method of claim 9 including the steps of:

reinserting the inner cannula in the outer cannula; and collecting a second tissue sample without having to puncture the skin of the body a second time.

11. A biopsy needle set comprising:

an outer cannula with a first longitudinal body and a first longitudinal axis;

an inner cannula with a second longitudinal body and a second longitudinal axis;

said outer cannula having an outer distal end with an outer opening with a length along the first longitudinal body;

said inner cannula having an inner distal end with an inner opening with a length along the second longitudinal body;

said inner cannula rotatably mounted inside said outer cannula with the first and second longitudinal axis being substantially co-linear;

said needle set having an open position wherein said inner opening is located adjacent said outer opening, and a closed position wherein said outer cannula covers the inner opening;

said outer cannula has an outer distal tip;

said inner cannula has an inner distal tip which mates inside of the outer distal tip and is held in place Inside the outer distal tip in order to allow the inner cannula and the outer cannula to rotate relative to each other;

said outer opening of said outer cannula has a first cutting edge thereon;

said inner opening of said inner cannula has a second cutting edge thereon;

wherein said outer opening extends to about one-half of a diameter of the first longitudinal body from the outer distal tip of the outer cannula and for the length of the outer opening; and said inner opening extends about one-half of a diameter of the second longitudinal body from the inner distal tip of the inner cannula and for the length of the inner opening so that with the needle set In said open position, the inner distal tip rests in the outer distal tip; and wherein the first and second cutting edge are without serrations in order to facilitate the slicing off of tissue as the needle set is urged past tissue along a direction co-linear with the first and second longitudinal axis.

12. The needle set of claim 11 wherein:

said first cutting edge and said second cutting edge are oriented so that, in a plane which is substantially perpendicular to the first and second longitudinal axis, said edges slope toward each other in order, together, to form a "V" shaped edge.

13. A biopsy needle set comprising:

an outer cannula with a first longitudinal body and a first longitudinal axis;

an inner cannula with a second longitudinal body and a second longitudinal axis with the first and second longitudinal axis being substantially co-linear;

said outer cannula having an outer distal end with an outer opening;

said inner cannula having an inner distal end with an inner opening;

said inner cannula rotatably mounted inside said outer cannula said needle set having an open position wherein said inner opening is located adjacent said outer opening, and a closed position wherein said outer cannula covers the inner opening;

said outer cannula has an outer distal tip;

said inner cannula has an inner distal tip which mates inside of the outer distal tip and is held in place inside the outer distal tip in order to allow the inner cannula and the outer cannula to rotate relative to each other;

said outer opening of said outer cannula has a first cutting edge thereon;

said inner opening of said inner cannula has a second cutting edge thereon; and said first cutting edge and said second cutting edge are oriented so that in a plane which is substantially perpendicular to the first and second longitudinal axis, said edges slope toward each other in order, together, to form a "V" shaped edge.

* * * * *